United States Patent [19]

Nakagawa et al.

[11] Patent Number: 5,760,278
[45] Date of Patent: Jun. 2, 1998

[54] STABILIZATION METHOD OF VINYL COMPOUND WITH HYDROXY GROUP AND COMPOSITION CONTAINING SUCH VINYL COMPOUND

[75] Inventors: Koichi Nakagawa; Mitsuaki Makino, both of Himeji; Yuichi Kita, Akashi, all of Japan

[73] Assignee: Nippon Shokubai Co., Ltd., Osaka, Japan

[21] Appl. No.: 711,206

[22] Filed: Sep. 9, 1996

[30] Foreign Application Priority Data

Sep. 14, 1995 [JP] Japan ................................. 7-237440

[51] Int. Cl.⁶ ................................................. C07C 69/73
[52] U.S. Cl. ........................ 560/183; 558/451; 562/579; 508/415; 508/496
[58] Field of Search .................. 562/579; 560/183; 558/451; 508/415, 490

[56] References Cited

U.S. PATENT DOCUMENTS 3,959,358  5/1976  Jursich ................................. 260/486

FOREIGN PATENT DOCUMENTS 0 669 312 A1  8/1995  European Pat. Off. .

OTHER PUBLICATIONS

Villieras et al., "Ethyl α-(Hydroxymethyl)Acrylate", *Organic Syntheses*, vol. 66, pp. 220–225, 1988.
"Dictionary of Organic Compounds" (Chapman and Hall, Fifth Edition, Second Supplement, p. 259, published 1984).

Primary Examiner—Paul J. Killos
Attorney, Agent, or Firm—Kubovcik & Kubovcik

[57] ABSTRACT

A stabilization method of a vinyl compound with hydroxy group of an improved stability is achieved by preventing it from being denatured on storage, transportation, manufacturing process while maintaining its reactivity. A composition containing the vinyl compound with hydroxy group of an improved stability is obtained by the described stabilization method. The stabilization method is characterized by coexisting a vinyl compound with hydroxy group of formula (1), a primary antioxidant, alcohol and/or water, $$CH_2=\underset{X}{\underset{|}{C}}-\underset{R}{\underset{|}{CH}}-OH \qquad (1)$$

wherein R is a hydrogen atom or an organic residue, X is a —CN group, a —$COR_0$ group or a —$COOR_0$ group, and $R_0$ is a hydrogen atom or an organic residue. In this stabilization method, not less than 50 ppm of alcohol and/or water is added with respect to the vinyl compound with hydroxy group. The stabilization method may be achieved by coexisting the above-defined vinyl compound with hydroxy group, the primary antioxidant and organic acid. In this case, not less than 10 ppm of organic acid is added to the vinyl compound with hydroxy group.

32 Claims, No Drawings

STABILIZATION METHOD OF VINYL COMPOUND WITH HYDROXY GROUP AND COMPOSITION CONTAINING SUCH VINYL COMPOUND

FIELD OF THE INVENTION

The present invention generally relates to a stabilization method of a vinyl compound with hydroxy group and a composition containing such vinyl compound, and more particularly relates to a stabilization method which offers an improved stability of the vinyl compound with hydroxy group by preventing a vinyl compound with hydroxy group from being denatured on storage, transportation, manufacturing process, etc., and to a composition containing the vinyl compound of an improved stability.

The vinyl compound with hydroxy group having an active hydroxyl group is a useful compound in a variety of fields, for example, as a monomer for use in preparing a polymer of high heat-resistance; a raw material for optical materials of high refractive index; raw materials for various chemical products, such as a coating agent, an adhesive agent, a builder for detergent, an improving agent for wood; an intermediate of medical supplies, such as an anticancer drug, an antivirus drug, etc.

BACKGROUND OF THE INVENTION

A vinyl compound with hydroxy group is a monomer having an active hydroxyl group, and it is generally known that such vinyl compound is heat-unstable. For this undesirable feature, the vinyl compound with hydroxy group generates an oligomer thereof when heated to or above room temperature, and further a thermal polymerization of the vinyl compound with hydroxy group is apt to occur only by heating it above room temperature. With a further application of heat, a glassy colorless transparent high polymer compound (polymer) is generated. Especially, a high purity vinyl compound with hydroxy group may cause a polymerization reaction based on a reactivity of the hydroxyl group even on its storage at room temperature, and generate impurities of high boiling point. Namely, if the vinyl compound with hydroxy group is stored for a long period of time at room temperature, impurities are generated which gradually lowers the quality of the vinyl compound.

For example, intensive studies have been made by the inventors of the present invention on the stability of α-(hydroxymethyl) acrylic esters. As a result, they have found that the α-(hydroxymethyl) acrylic esters have a highly active methylol group and a double bond. Therefore, when the α-(hydroxymethyl) acrylic esters are stored for a long period of time at room temperature, impurities that are assumed to be generated by reacting an oligomer of α-(hydroxymethyl) acrylic esters and a methylol group to a double bond by Michael additive reaction, impurities of unknown structure, etc., are gradually generated. As a result, they have found that when the α-(hydroxymethyl)alkyl acrylate is stored for a long period of time at room temperature, impurities are generated which results in lower purity.

On the other hand, in order to achieve an improved stability of a heat-unstable compound, conventionally, a polymerization inhibitor such as p-methoxyphenol, hydroquinone, phenothiazine, p-t-butylcatechol, etc., is added to the compound as a stabilizer.

However, the described stabilization method of the heat-unstable compound by adding the stabilizer has the following drawbacks. That is, the main purpose of adding such stabilizer is to improve the heat-stability of the vinyl group. Therefore, although the stabilization effect is fully anticipated for the compound having a vinyl group, it is not effective for the compound having other functional group. Namely, the effect of the described stabilizer greatly varies depending on the structure of the compound. For this reason, in the described conventional stabilization method, even if the stabilizer is added in a large amount, it is not necessarily that the sufficient stabilization effect for the vinyl compound with hydroxy group can be expected. Besides, if the stabilizer is added in a large amount, the reactivity of the vinyl compound with hydroxy group cannot be maintained, and this have led to the need for development of a desirable stabilization method for the vinyl compound with hydroxy group. On the other hand, if a large amount of hydroquinone is added as a stabilizer, a compound would be colored over time.

SUMMARY OF THE INVENTION

The first object of the present invention is to provide a stabilization method for a vinyl compound with hydroxy group by preventing it from being denatured on storage, transportation, manufacturing process, etc., while maintaining its reactivity.

The second object of the present invention is to provide a composition containing a vinyl compound with hydroxy group of an improved stability.

In order to achieve the above object, intensive studies have been made by the inventors of the present invention on the stabilization method for the vinyl compound with hydroxy group, and a composition containing the vinyl compound with hydroxy group of an improved stability. As a result, they have found that with a coexistence of a vinyl compound with hydroxy group, the primary antioxidant, alcohol and/or water, or by a coexistence of the vinyl compound with hydroxy group, the primary antioxidant and the organic acid, the vinyl compound with hydroxyl group can be prevented from being denatured on storage, transportation, manufacturing process, etc., while maintaining its reactivity, thereby achieving an improved stability of the vinyl compound with hydroxy group to complete the present invention.

Namely, in order to achieve the first object of the present invention, the stabilization method of the vinyl compound with hydroxy group in accordance with the present invention is characterized by including the step of:

(a) coexisting a vinyl compound with hydroxy group of formula (1), a primary antioxidant, alcohol and/or water,

wherein R is a hydrogen atom or an organic residue, X is a —CN group, a —COR$_0$ group or a —COOR$_0$ group, and R$_0$ is a hydrogen atom or an organic residue.

Another stabilization method of vinyl compound with hydroxy group of the present invention is characterized by including the step of coexisting the vinyl compound with hydroxy group of formula (1), the primary antioxidant, and the organic acid.

According to the stabilization method of the present invention, the vinyl compound with hydroxy group can be prevented from being denatured on storage, transportation and manufacturing process while maintaining its reactivity. As a result, an improved stability of the vinyl compound with hydroxy group can be achieved. Another benefit of the stabilization method of the present invention lies in that it does not adversely affect the reactivity of the vinyl compound with hydroxy group which eliminates the need of refining the vinyl compound with hydroxy group. For the described beneficial features, the stabilization method of the present invention is industrially useful.

In order to achieve the second object, the composition containing the vinyl compound with hydroxy group of the present invention is characterized by including the vinyl compound with hydroxy group of formula (1), the primary antioxidant, and alcohol and/or water.

Another composition including the vinyl compound with hydroxy group of the present invention is characterized by including the vinyl compound with hydroxy group of formula (1), the primary antioxidant, and organic acid.

The vinyl compound with hydroxy group of the described structure offers an improved stability. Moreover, when manufacturing derivatives or polymers of the vinyl compound with hydroxy group, the described composition permits the side reaction of the vinyl compound with hydroxy group to be suppressed. Moreover, as the described stabilization method does not adversely affect the reactively of the vinyl compound with hydroxy group, the need of the refining process can be omitted. For the described beneficial features, the stabilization method of the present invention is industrially useful.

For a fuller understanding of the nature and advantages of the invention, reference should be made to the ensuing detailed description taken in conjunction with the accompanying drawings.

DESCRIPTION OF THE EMBODIMENTS

The present invention will now be described in further detail.

A vinyl compound with a hydroxyl group represented by the formula (1) of the present invention is easily obtained by a reaction of a vinyl compound of the formula (2) and an aldehyde compound,

wherein X is a —CN group, a —COR$_0$ group, or a —COOR$_0$ group, and R$_0$ is a hydrogen atom or an organic residue. The method of manufacturing a vinyl compound with hydroxy group is not particularly limited.

The vinyl compound of the formula (2) has a substituent X of a —CN group, a —COR$_0$ group or a —COOR$_0$ group, and a substituent R$_0$ of a hydrogen atom or an organic residue. Examples of the vinyl compound include acrylonitrile having a substituent X of a —CN group, alkyl vinylketone having a substituent X of a COR$_0$ group, acrylic ester having a substituent X of a —COOR$_0$ group, etc. Among these vinyl compounds, acrylic esters are especially preferable.

The substituent R$_0$ specifically indicates a hydrogen atom, an alkyl group of 1 to 18 carbon atoms, a cycloalkyl group of 3 to 10 carbon atoms, an aryl group, a hydroxyalkyl group of 1 to 8 carbon atoms, a —(CH$_2$)$_m$NR$_1$R$_2$ group, a —(CH$_2$)$_m$N$^+$R$_1$R$_2$R$_3$—M$^-$ group, or a —(C$_2$H$_4$O)$_n$R$_4$ group. The substituents R$_1$, R$_2$ and R$_3$ are independently straight chain or branched chain alkyl group of 1 to 8 carbon atoms, m is an integer of 2 to 5. An anion M$^-$ specifically indicates Cl$^-$, Br$^-$, CH$_3$COO$^-$, HCOO$^-$, SO$_4^{2-}$, or PO$_4^{3-}$. A substituent R$_4$ is a straight chain or branched chain alkyl group of 1 to 18 carbon atoms, and n is an integer of 1 to 80.

Examples of alkyl vinyl ketone include: methyl vinyl ketone, ethyl vinyl ketone, isopropyl vinyl ketone, butyl vinyl ketone, cyclohexyl vinyl ketone, phenyl vinyl ketone, acrolein, etc. Among these alkyl vinyl ketones, methyl vinyl ketone and isopropyl vinyl ketone are especially preferable.

Suitable acrylic esters include:
(a) acrylic acid having a substituent R$_0$ of a hydrogen atom;
(b) alkyl acrylate having a substituent R$_0$ of 1 to 18 carbon atoms such as methyl acrylate, ethyl acrylate, n-propyl acrylate, isopropyl acrylate, n-butyl acrylate, isobutyl acrylate, tert-butyl acrylate, n-octyl acrylate, iso-octyl acrylate, 2-ethylhexyl acrylate, lauryl acrylate, or stearyl acrylate;
(c) cycloalkyl acrylate having a substituent R$_0$ of a cycloalkyl group of 3 to 10 carbon atoms such as cyclopentyl acrylate, or cyclohexyl acrylate;
(d) aryl acrylate having a substituent R$_0$ of an aryl group such as phenyl acrylate, o-methoxyphenyl acrylate, p-methoxyphenyl acrylate, p-nitrophenyl acrylate, o-methylphenyl acrylate, p-methylphenyl acrylate, or p-tert-butylphenyl acrylate;
(e) hydroxyalkyl acrylate having a substituent R$_0$ of a hydroxyalkyl group of 1 to 8 carbon atoms such as 2-hydroxyethyl acrylate, 2-hydroxypropyl acrylate, 3-hydroxypropyl acrylate, or 4-hydroxybutyl acrylate;
(f) aminoalkyl acrylate having a substituent R$_0$ of a —(CH$_2$)$_m$NR$_1$R$_2$ group such as N,N-dimethylaminoethyl acrylate, N,N-diethylaminoethyl acrylate, N,N-dimethylaminopropyl acrylate, N,N-diethylaminopropyl acrylate, N,N-dimethylaminobutyl acrylate, N,N-diethylaminobutyl acrylate, N,N-dimethylaminoneopentyl acrylate, or N,N-diethylaminoneopentyl acrylate;
(g) quaternary ammonium compound of aminoalkyl acrylate having a substituent R$_0$ of a —(CH$_2$)$_m$N$^+$R$_1$R$_2$R$_3$—M$^-$ group such as quaternary ammonium compound of N,N-dialkylaminoalkyl acrylate; and
(h) acrylic ester having a substituent R$_0$ of a —(C$_2$H$_4$O)$_n$R$_4$ group such as methoxyethyl acrylate, ethoxyethyl acrylate, lauryl oxytrioxyethyl acrylate, and methoxypolyoxyethylene acrylate wherein n is between 1 and 80, more preferably, between 3 and 30.

Among these acrylic esters, methyl acrylate, ethyl acrylate, n-butyl acrylate, 2-ethylhexyl acrylate, 2-hydroxyethyl acrylate, and 2-hydroxypropyl acrylate are especially preferable.

Examples of aldehyde series compound include: compounds containing an aldehyde group; trioxane; paraacetoaldehyde; and an oxymethylene compound of the general formula (3)

wherein Y is a hydrogen atom, a straight-chain or branched-chain alkyl group of 1 to 8 carbon atoms, or a cycloalkyl group of 3 to 10 carbon atoms, and p is an integer of 1 to 100. When the substituent Y in the general formula (3) is a cycloalkyl group of 3 to 10 carbon atoms, the cycloalkyl group may further contain another substituent.

Examples of such compound having an aldehyde group include: formaldehyde, acetoaldehyde, propionaldehyde, butylaldehyde, valeraldehyde, isobutylaldehyde, pivalynaldehyde, cyclohexylaldehyde, cyclohexenealdehyde, benzaldehyde, tolualdehyde, anisaldehyde, and furfural.

The oxymethylene compound is, for example, formaldehyde, paraformaldehyde that is a polymer (8 to 100 moles) of formaldehyde, etc.

By reacting the vinyl compound with the aldehyde series compound, the target vinyl compound with hydroxy group of the general formula (1) is obtained. The vinyl compound with hydroxy group is a compound of the general formula (1), wherein X is the same as the above-mentioned substituent, and R is a hydrogen atom or an organic residue. Specifically, the substituent R is, for example, a hydrogen atom, an alkyl group of 1 to 18 carbon atoms, an aryl group, or a heterocyclic group. Among the above-listed compounds, for the vinyl compound with hydroxy group, acrylic ester compounds are especially preferable. The substituent R is a substituent derived from the aldehyde series compound.

Examples of the primary antioxidant for the stabilization method of the present invention include:

(a) substituted phenol such as p-methoxyphenol, 2,6-di-t-butyl-4-methylphenol, 2-6-di-t-butyl-4-ethyl phenol, 2,4-di-t-butylphenol, 2,4,6-tri-t-butylphenol, 2,2'-methylene-bis-(4-methyl-6-t-butylphenol), 2, 2'-methylene-bis-(4-ethyl-6-t-butylphenol), 4,4'-butylidene-bis-(3-methyl-6-t-butylphenol), 4,4'-thio-bis-(3-methyl-6-t-butylphenol), n-octadecyl-3-(4-hydroxy-3,5-di-t-butylphenol) propyonate, 3,3-bis-(3-t-butyl-4-hydroxyphenyl)ethylate, tetrakis-[methylene-3-(3,5-di-t-butyl-4-hydroxyphenyl) propionate] methane, triethyleneglycol-bis-[3-(3-t-butyl-5-methyl-4-hydroxyphenyl)propyonate], pentaerithrichil-tetrakis[3-(3,5-di-t-butyl-4-hydroxyphenyl) propyonate], 1,6-hexanediol-bis-[3-(3,5-di-t-butyl-4-hydroxyphenyl) propyonate], etc.;

(b) substituted catechol such as p-t-butylcatechol;

(c) substituted hydroquinone such as 2-methyl hydroquinone, 2-t-butyl hydroquinone, 2,5-di-t-butyl hydroquinone, 2,5-di-t-alminohydroquinone;

(d) substituted resorcin;

(e) phenochiazin; and (f) acrylic ester (substituted acrylate) such as [2-t-butyl-6-(3-t-butyl-2-hydroxy-5-methylbenzil)-4-methylphenyl] acrylate, [2-{1-(2-hydroxy-3,5-dipentylphenyl)ethyl}-4,6-di-t-pentylphenyl], acrylate, etc.

Only one kind of the above-listed primary antioxidant may be adopted, or two or more kinds thereof may be suitably mixed and adopted. Among the above-listed compounds, p-methoxyphenol, p-t-butyl catechol, and phenothiazine are especially preferable.

An amount of additive of the primary antioxidant with respect to the vinyl compound with hydroxy group is not particularly limited, and is suitably adjusted in consideration of the kind of the vinyl compound with hydroxy group, the kind of the primary antioxidant, an amount of use of alcohol and/or water or an amount of use of organic acid. Specifically, the primary antioxidant is typically added in an amount ranging from 10 ppm to 5,000 ppm with a more preferred range being from 50 ppm to 1,000 ppm and the most preferred range being from 100 ppm to 500 ppm. When the primary antioxidant is used in the described range, the performance of the primary antioxidant can be fully anticipated, thereby achieving an improved stability of the vinyl compound with hydroxy group. If the primary antioxidant is used in an amount of less than 10 ppm, the generation of impurities (especially, oligomer) may not be fully suppressed. On the other hand, if the primary antioxidant is used in an amount above 5,000 ppm, an improved effect of suppressing the generation of the impurities cannot be expected. This means that a part of the primary antioxidant is wasted. Thus, it is not economically advantageous to use the primary antioxidant more than the described range.

Examples of alcohol used in the stabilization method of the present invention include: methanol, ethanol, n-propanol, isopropanol, n-butanol, t-butanol, n-hexanol, cyclohexanol, 2-ethylhexanol, methyleneglycol (methanediol), polyoxymethyleneglycol, ethyleneglycol, propyleneglycol, polyethyleneglycol, polypropyleneglycol, methylcellosolve, ethylcellosolve, isopropylcellosolve, methoxymethanol, ethoxymethanol, etc. The alcohol of the present invention is not limited to the above-listed compounds. Only one kind of the above-listed alcohol may be adopted, or two or more kinds thereof may be suitably mixed and adopted. Namely, in the stabilization method of the present invention, water, at least one kind of alcohol, or a mixture of water and at least one kind of alcohol may be used.

In the coexistence of the vinyl compound with hydroxy group and alcohol and/or water, the ratio of alcohol and/or water with respect to the vinyl compound with hydroxy group is not particularly limited, and is suitably adjusted in consideration of the kind of the vinyl compound with hydroxy group, the kind or the combination of alcohol and/or water, the amount of use of the primary antioxidant, and the form in using of the vinyl compound with hydroxy group, etc. The amount of use of alcohol and/or water with respect to the vinyl compound with hydroxy group preferably has a lower limit of 50 ppm ($5\times10^{-5}$ times by weight) and an upper limit of 100 times by weight.

In the case where alcohol and/or water coexists as additives to stabilize the vinyl compound with hydroxy group, it is especially preferable that alcohol and/or water is used with respect to the vinyl compound with hydroxy group in an amount ranging from 50 ppm to 5,000 ppm, with most preferred range being from 100 ppm to 1,000 ppm.

In the case of stabilizing the vinyl compound with hydroxy group in the form of the solvent of alcohol and/or water, it is preferable to mix alcohol and/or water in an amount ranging from above 5,000 ppm ($5\times10^{-3}$ times by weight) to not more than 100 times by weight, with the most preferred range being from 0.1 times by weight to 10 times by weight. Namely, when forming alcohol or water solution of the vinyl compound with a hydroxyl group, the vinyl compound preferable has a concentration of around 10 percent by weight to 90 percent by weight.

As a result, a still improved stability of the vinyl compound with hydroxy group can be achieved. If the alcohol or water is used in an amount less than 50 ppm, the generation of impurities cannot be fully suppressed, and causes the problem that the quality is lowered, for example, on storage at around room temperature, etc., thereby presenting the problem that the stability of the vinyl compound with hydroxy group cannot be improved significantly.

By the coexistence of the vinyl compound with hydroxy group, the primary antioxidant, alcohol and/or water, the composition of the present invention, i.e., the composition containing a vinyl compound with a hydroxyl group can be obtained. The composition of the present invention may further include a stabilizer such as sulfur, thioether, phosphate, phosphite, etc., as occasion demands. As an improved protection against denaturation of the vinyl compound with hydroxyl group can be achieved by adding the stabilizer, a still improved stability of the vinyl compound with hydroxy group can be achieved.

The method of coexisting the vinyl compound with hydroxy group, the primary antioxidant, alcohol and/or water is not particularly limited. For example, the primary antioxidant, alcohol and/or water may be added or mixed in the high purity vinyl compound with hydroxy group in the above-defined amounts. Alternatively, after adding or mixing a predetermined amount of the primary antioxidant, alcohol and/or water to the vinyl compound containing a coarse hydroxyl group, the respective amounts of use of the primary antioxidant and alcohol and/or water are adjusted with respect to the vinyl compound with hydroxy group by refining (distilling, etc.,) in the manufacturing process.

Examples or organic acid to be adopted in the stabilization method of the present invention include:

(a) monobasic acid such as (meth)acrylic acid, formic acid, acetic acid, butyric acid, phenol, substituted phenol, etc.;
(b) dibasic acid such as fumaric acid, terephthalic acid, succinic acid, maleic acid, etc.; and
(c) polybasic acid such as trimellitic acid, pyromellitic acid, butanetetracarboxylic acid, etc.

However, the organic acid to be adopted in the stabilization method of the present invention is not limited to the above-listed compounds. Only one kind of such organic acid may be used, or two or more kinds thereof may be suitably mixed and adopted.

The amount of use of the organic acid with respect to the vinyl compound with hydroxy group is not particularly limited and should be suitably adjusted in consideration of the kind of the vinyl compound with hydroxy group, the kind of the organic acid, and an amount of the primary antioxidant, etc. specifically, the organic acid is typically used in an amount above 10 ppm, with more preferred range being from 10 ppm to 5,000 ppm and the most preferred range being from 50 ppm to 1,000 ppm. As a result, a still improved stability of the vinyl compound with hydroxy group can be achieved. If the organic acid is used in an amount less than 10 ppm, the generation of the impurities cannot be fully suppressed, which results in a deterioration of the quality on storage, for example, at room temperature, thereby presenting the problem that the stability of the vinyl compound with hydroxy group cannot be achieved.

The coexistence of the described vinyl compound with hydroxy group, the primary antioxidant and organic acid provide the composition of the present invention, i.e., the composition of the vinyl compound with hydroxy group. The composition may include the stabilizer such as sulfur, thioether, phosphate, phosphite as occasion demands. As an improved protection against the denaturation of the vinyl compound with hydroxy group can be achieved by adding these stabilizer, an still improved stability of the vinyl compound with hydroxy group can be achieved.

The method of coexisting the vinyl compound of the hydroxyl group, the primary antioxidant and the organic acid is not particularly limited. For example, the primary antioxidant and the organic acid may be added in the aforementioned amount range to the high purity vinyl compound with hydroxy group. Or after adding or mixing a predetermined amount of the primary antioxidant and the organic acid to the vinyl compound containing a coarse hydroxyl group, the amount of the primary antioxidant and the organic acid may be adjusted with respect to the vinyl compound with hydroxy group by refining (i.e., distilling, etc.) in the manufacturing process. Here, a combined use of the organic acid and alcohol and/or water is permitted.

While coexisting the vinyl compound with hydroxy group, the primary antioxidant, and alcohol and/or water, or coexisting the vinyl compound with hydroxy group, the primary antioxidant and organic acid, the oxygen concentration in the atmosphere in which these compounds are treated typically has a concentration ranging from 1 volume percent to 30 volume percent, with more preferred range being from 5 volume percent to 25 volume percent. As a result, a still improved stability of the vinyl compound with hydroxy group can be achieved. The atmosphere in which the described compounds are treated is not limited; however, may be treated in a mixed gas atmosphere of inactive gas such as nitrogen, argon, etc., and oxygen.

When treating the composition containing the vinyl compound with hydroxy group, the concentration of oxygen in the gaseous phase portion of the container in which the composition is sealed is adjusted to the aforementioned amount range. As a result, a still improved stability of the vinyl compound with hydroxy group can be achieved. The method of adjusting the concentration of oxygen in the gaseous phase portion is not particularly limited but, for example the method of introducing an inactive gas such as nitrogen, argon, etc., into the gaseous phase portion, the method of substituting the gaseous phase portion using the mixed gas atmosphere of inactive gas and oxygen may be adopted.

As described, one example method of stabilizing the vinyl compound with hydroxy group in accordance with the present invention is characterized by coexisting the vinyl compound with hydroxy group of formula (1), the primary antioxidant and alcohol and/or water. Another example method of stabilizing the vinyl compound with hydroxy group in accordance with the present invention is characterized by coexisting the vinyl compound with hydroxy group of formula (1), the primary antioxidant and organic acid.

The described method of the present invention prevents the vinyl compound with hydroxy group from being denatured on storage, transportation, manufacturing process, etc., while maintaining its reactivity. As a result, an improved stability of the vinyl compound with hydroxy group can be achieved. Moreover, as the described stabilization method does not adversely affect the reactively of the vinyl compound with hydroxy group, the need of the refining process can be omitted. For the described beneficial features, the stabilization method of the present invention is industrially useful.

As described, the composition of the vinyl compound with hydroxy group of the present invention includes the vinyl compound with hydroxy group of formula (1), the primary antioxidant and alcohol and/or water. Another composition of the vinyl compound containing a hydroxyl group of formula (1) includes the primary antioxidant and organic acid.

The vinyl compounds with hydroxy group of the described structures offer an improved stability. Additionally, when manufacturing the derivatives or polymers of the vinyl compound with hydroxy group, the described composition suppresses the side reaction of the vinyl compound with hydroxy group. Namely, as the composition does not adversely affect the reactivity of the vinyl compound with hydroxy group, the need of the refining process of the vinyl compound with hydroxy group is eliminated. For the described beneficial features, the composition of the vinyl compound with hydroxy group of the present invention is industrially useful.

In order that the invention may be more readily understood, the following non-limiting examples and comparative examples are given.

EXAMPLE 1

In a 200-ml glass vessel that can be sealed, placed was 100 g of refined ethyl α-(hydroxymethyl) acrylate by distillation (boiling point: 70° C. to 72° C./5 Torr; hereinafter referred to as EHMA) as a vinyl compound with hydroxy group. Then, to the EHMA, added were p-methoxylphenol (primary antioxidant) and water respectively in amounts of 300 ppm and 1,000 ppm with respect to the EHMA, to prepare a composition. Further, the oxygen in the gaseous phase portion of the glass vessel was adjusted to have a concentration of 21 volume percent. The resulting composition was observed to be colorless transparent solution. The amounts of the described additives are shown in Table 1.

After sealing the glass vessel in which the resulting composition was placed, the glass vessel was placed still in a thermostatic bath whose temperature is controlled at 50°±2° C., and changes in EHMA over time, i.e., the stability thereof was evaluated. Specifically, the ratio (percent by weight) of the residual EHMA in the composition was measured using the gas chromatography (GC) twice after placing the bottle still in the thermostatic bath for four weeks and eight weeks. Further, the appearance of the composition after an elapsed of eight weeks was observed, and was analyzed using the gel permeation chromatography (GPC) to see if an oligomer and a high molecular compound (polymer) was generated. The measurement by the GPC was carried out on a column of SHODEX A-802 (available from Showa Denko Co., Ltd.) and a moving phase of tetrahydrofuran (THF) using a UV detector and a refractive index (RI) detector.

As a result, the ratio of the residual EHMA in the composition was found to be 100 percent by weight both after elapsed of four weeks and eight weeks. The composition was observed to be colorless transparent solution. In the GPC chart, the respective peaks of the oligomer and the high molecular compound were not observed. The results are summarized in Table 2.

EXAMPLE 2

Example 1 was repeated except that in replace of water, ethanol (alcohol) was added in an amount of 1,000 ppm with respect to the EHMA to prepare a composition. The amounts of the additives are shown in Table 1. Next, using the resulting composition, the stability of the EHMA was evaluated in the same manner as in Example 1. The results are summarized in Table 2.

EXAMPLE 3

Example 1 was repeated except that water was added in an amount of 50 ppm, and ethanol was added in an amount of 500 ppm with respect to the EHMA to prepare a composition. The amounts of the additives are shown in Table 1. Next, using the resulting composition, the stability of the EHMA was evaluated in the same manner as in Example 1. The results are summarized in Table 2.

EXAMPLE 4

Example 1 was repeated except that water was added in an amount of 100 ppm, and ethoxymethanol (alcohol) was added in an amount of 500 ppm with respect to the EHMA to prepare a composition. The amounts of the additives are shown in Table 1. Next, using the resulting composition, the stability of the EHMA was evaluated in the same manner as in Example 1. The results are summarized in Table 2.

EXAMPLE 5

Example 4 was repeated except that in replace of ethoxymethanol, methoxymethanol (alcohol) was added in an amount of 500 ppm with respect to the EHMA to prepare a composition. The amounts of the additives are shown in Table 1. Next, using the resulting composition, the stability of the EHMA was evaluated in the same manner as in Example 1. The results are summarized in Table 2.

EXAMPLE 6

Example 1 was repeated except that in replace of p-methoxyphenol, p-t-butylcatechol (primary antioxidant) was added in an amount of 100 ppm, and water and ethanol were added respectively in an amount of 100 ppm with respect to the EHMA to prepare a composition. Further, the oxygen in the gaseous phase portion of the glass vessel was adjusted to have a concentration of 15 volume percent. The amounts of the additives are shown in Table 1. Next, using the resulting composition, the stability of the EHMA was evaluated in the same manner as in Example 1. The results are summarized in Table 2.

EXAMPLE 7

Example 1 was repeated except that in replace of p-methoxyphenol, 2-t-butyl hydroquinone (primary antioxidant) was added in an amount of 100 ppm, and water and ethanol were added respectively in amounts of 500 ppm and 100 ppm with respect to the EHMA to prepare a composition. Further, the oxygen in the gaseous phase portion of the glass vessel was adjusted to have a concentration of 7 volume percent. The amounts of the additives are shown in Table 1. Next, using the resulting composition, the stability of the EHMA was evaluated in the same manner as in Example 1. The results are summarized in Table 2.

EXAMPLE 8

In the same glass vessel as described in Example 1, placed was 100 g of refined methyl α-(hydroxymethyl) acrylate by distillation (hereinafter referred to as MHMA) as a vinyl compound with hydroxy group. Then, to the MHMA, added were p-methoxylphenol, water and methoxymethanol respectively in amounts of 500 ppm, 200 ppm and 100 ppm with respect to the MHMA, to prepare a composition. Further, the oxygen in the gaseous phase portion of the glass vessel was adjusted to have a concentration of 21 volume percent. The composition was observed to be colorless transparent solution. The amounts of the described additives are shown in Table 1. The amounts of the additives are shown in Table 1. Next, using the resulting composition, the stability of the MHMA was evaluated in the same manner as in Example 1. The results are summarized in Table 2.

EXAMPLE 9

In the same glass vessel as described in Example 1, placed was 100 g of refined n-butyl α-(hydroxymethyl) acrylate by distillation (hereinafter referred to as BHMA) as a vinyl compound with hydroxy group. Then, to the BHMA, added were p-methoxylphenol and water respectively in amounts of 100 ppm and 50 ppm with respect to the BHMA, and n-butanol (alcohol) in an amount of 50 ppm to prepare a composition. Further, the oxygen in the gaseous phase portion of the glass vessel was adjusted to have a concentration of 21 volume percent. The composition was observed to be colorless transparent solution. The amounts of the described additives are shown in Table 1. The amounts of the additives are shown in Table 1. Next, using the resulting composition, the stability of the BHMA was evaluated in the same manner as in Example 1. The results are summarized in Table 2.

EXAMPLE 10

In the same glass vessel as described in Example 1, placed was 100 g of refined α-(hydroxymethyl) acrylonitrile by distillation (hereinafter referred to as HMAN) as a vinyl compound with hydroxy group. Then, to the HMAN, added were p-methoxylphenol and water respectively in amounts of 300 ppm and 1,000 ppm with respect to the HMAN, to prepare a composition. Further, the oxygen in the gaseous phase portion of the glass vessel was adjusted to have a concentration of 21 volume percent. The composition was observed to be colorless transparent solution. The amounts of the described additives are shown in Table 1. The amounts of the additives are shown in Table 1. Next, using the resulting composition, the stability of the HMAN was evaluated in the same manner as in Example 1. The results are summarized in Table 2.

COMPARATIVE EXAMPLE 1

Example 1 was repeated except that p-methoxyphenol and water were not added to prepare a comparative composition. Namely, EHMA described in Example 1 was used as a comparative composition. Then, the stability of the EHMA was evaluated in the same manner as in Example 1. The results are summarized in Table 2. The ratio of the residual EHMA became 0 percent by weight after 4 weeks, and therefore, the EHMA was fairly unstable.

COMPARATIVE EXAMPLE 2

Example 1 was repeated except that water was not added to prepare a comparative composition. The amounts of the additives are shown in Table 1. Next, using the resulting composition, the stability of the EHMA was evaluated in the same manner as in Example 1. The results are summarized in Table 2.

COMPARATIVE EXAMPLE 3

In the same glass vessel as described in Example 1, placed was 100 g of EHMA. Then, to the EHMA, added were hydroquinone (stabilizer) and ethanol respectively in amounts of 300 ppm and 10 ppm with respect to the EHMA to prepare a comparative composition. Further, the oxygen in the gaseous phase portion of the glass vessel was adjusted to have a concentration of 21 volume percent. The comparative composition was observed to be colorless transparent solution. The amounts of the described additives are shown in Table 1. Next, using the resulting composition, the stability of the EHMA was evaluated in the same manner as in Example 1. The results are summarized in Table 2.

COMPARATIVE EXAMPLE 4

In the same glass vessel as described in Example 1, placed was 100 g of EHMA. Then, to the EHMA, added were water and ethanol respectively in amounts of 5,000 ppm with respect to the EHMA to prepare a comparative composition. Further, the oxygen in the gaseous phase portion of the glass vessel was adjusted to have a concentration of 21 volume percent. The comparative composition was observed to be colorless transparent solution. The amounts of the described additives are shown in Table 1. Next, using the resulting composition, the stability of the EHMA was evaluated in the same manner as in Example 1. The results are summarized in Table 2.

TABLE 1

|  |  | vinyl compound with hydroxy group | primary antioxidant*1) (ppm) | water*1) (ppm) | alcohol*1) (ppm) | concentration of oxygen*2) |
|---|---|---|---|---|---|---|
| Ex. | 1 | EHMA | p-methoxy phenol 300 | 1,000 | — | 21 |
|  | 2 | EHMA | p-methoxy phenol 300 | — | ethanol 1,000 | 21 |
|  | 3 | EHMA | p-methoxy phenol 300 | 50 | ethanol 500 | 21 |
|  | 4 | EHMA | p-methoxy phenol 300 | 100 | ethoxy methanol 500 | 21 |
|  | 5 | EHMA | p-methoxy phenol 300 | 100 | methoxy methanol 500 | 21 |
|  | 6 | EHMA | p-t-butylcatechol 100 | 100 | ethanol 100 | 15 |
|  | 7 | EHMA | TBHQ 100 | 500 | methanol 100 | 7 |
|  | 8 | MHMA | p-methoxy phenol 500 | 200 | methoxy methanol 100 | 21 |
|  | 9 | BHMA | p-methoxy phenol 100 | 50 | n-butanol 50 | 21 |
|  | 10 | HMAN | p-methoxy phenol 300 | 1,000 | — | 21 |
| Com. Ex. | 1 | EHMA | — | — | — | 21 |
|  | 2 | EHMA | p-methoxy phenol 300 | — | — | 21 |
|  | 3 | EHMA | hydroquinone 300 | — | ethanol 10 | 21 |
|  | 4 | EHMA | — | 5,000 | ethanol 5,000 | 21 |

In the Table, EHMA: ethyl α-(hydroxymethyl) acrylate, MHMA: methyl α-(hydroxymethyl) acrylate, BHMA: n-butyl α-(hydroxymethyl) acrylate, HMAN: α-(hydroxymethyl) acrylonitrile, TBHQ: 2-t-butyl hydroquinone *1): amount with respect to the vinyl compound with hydroxy group *2): volume percent

TABLE 2

|  |  | after 4 weeks | after 8 weeks | | |
|---|---|---|---|---|---|
|  |  | *1) | *1) | appearance | GPC analysis result |
| Ex. | 1 | 100 | 100 | *2) | *7) |
|  | 2 | 100 | 97 | *2) | *7) |
|  | 3 | 100 | 98 | *2) | *7) |
|  | 4 | 100 | 98 | *2) | *7) |
|  | 5 | 100 | 98 | *2) | *7) |
|  | 6 | 100 | 98 | *2) | *7) |
|  | 7 | 100 | 99 | *2) | *7) |
|  | 8 | 100 | 98 | *2) | *7) |
|  | 9 | 100 | 99 | *2) | *7) |
|  | 10 | 100 | 99 | *2) | *7) |
| Com. Ex. | 1 | 0 | 0 | *3) | *8) |
|  | 2 | 100 | 89 | *4) | *9) |

TABLE 2-continued

| | after 4 weeks | after 8 weeks | | |
|---|---|---|---|---|
| | *1) | *1) | appearance | GPC analysis result |
| 3 | 100 | 91 | *5) | *9) |
| 4 | 95 | 30 | *6) | *10) |

In the table, *1) is a ratio of residual (percent by weight), *2) is a colorless transparent solution, *3) is glassy solid, *4) is slightly white turbid solution, *5) is slightly ivory colored transparent solution, *6) is white turbid solution, *7) indicated that no peak of the oligomer and the high molecular compound was observed, *8) indicates that a large peak of the high molecular compound was observed, *9) indicates that a peak of the oligomer was observed, and *10) indicates that two peaks of the oligomer and high molecular compound were observed.

EXAMPLE 11

In a predetermined volume of glass vessel that can be sealed, placed was 100 g of EHMA. Then, to the EHMA, added were p-methoxyphenol and water and ethanol respectively in an amount of 500 ppm and in an equivalent amount by weight (100 g) with respect to the EHMA to prepare a composition. Further, the oxygen in the gaseous phase portion of the glass vessel was adjusted to have a concentration of 21 volume percent. The resulting composition was observed to be colorless transparent solution. The mixed amount is shown in Table 3. Next, using the resulting composition, the stability of the EHMA was evaluated in the same manner as in Example 1. The results are summarized in Table 4.

EXAMPLE 12

In the same glass vessel as described in Example 11, placed was 100 g of EHMA. Then, to the EHMA, added were p-t-butylcatechol, water and ethanol respectively in an amount of 500 ppm, an amount of three times by weight (300 g), and an amount of 0.1 times by weight (10 g) with respect to the EHMA to prepare a composition. Further, the oxygen in the gaseous phase portion of the glass vessel was adjusted to have a concentration of 21 volume percent. The resulting composition was observed to be colorless transparent solution. The mixed amount is shown in Table 3. Next, using the resulting composition, the stability of the EHMA was evaluated in the same manner as in Example 1. The results are summarized in Table 4.

EXAMPLE 13

Example 11 was repeated except that ethanol was mixed in the EHMA in an amount of 9 times by weight (900 g) with respect to the EHMA to prepare a composition. The mixed amount is shown in Table 3. Next, using the resulting composition, the stability of the EHMA was evaluated in the same manner as in Example 1. The results are summarized in Table 4.

EXAMPLE 14

In the same glass vessel as described in Example 11, placed was 100 g of BHMA. Then, to the BHMA, added were p-methoxyphenol and propylene glycol (alcohol) respectively in an amount of 300 ppm and an equivalent amount by weight (100 g) with respect to the BHMA to prepare a composition. Further, the oxygen in the gaseous phase portion of the glass vessel was adjusted to have a concentration of 21 volume percent. The resulting composition was observed to be colorless transparent solution. The mixed amount is shown in Table 3. Next, using the resulting composition, the stability of the BHMA was evaluated in the same manner as in Example 1. The results are summarized in Table 4.

TABLE 3

| | | vinyl compound with hydroxy group | primary antioxidant*1) (ppm) | water*1) (times by weight) | alcohol*1) (ppm) (times by weight) | oxygen concentration (volume percent) |
|---|---|---|---|---|---|---|
| Ex | 11 | EHMA | p-methoxy phenol 500 | 1 | — | 21 |
| | 12 | EHMA | p-t-butylcatechol 500 | 3 | ethanol 0.1 | 21 |
| | 13 | EHMA | p-methoxy phenol 500 | — | ethanol 9 | 21 |
| | 14 | BHMA | p-methoxy phenol 300 | — | propylene glycol 1 | 21 |

In the Table, EHMA: ethyl α-(hydroxymethyl) acrylate, BHMA: n-butyl α-(hydroxymethyl) acrylate
*1)amount with respect to the vinyl compound with hydroxy group

TABLE 4

| | | after 4 weeks | after 8 weeks | | |
|---|---|---|---|---|---|
| | | *1) | *1) | appearance | GPC analysis result |
| Ex. | 11 | 98 | 96 | *2) | *7) |
| | 12 | 98 | 95 | *2) | *7) |
| | 13 | 100 | 98 | *2) | *7) |
| | 14 | 100 | 98 | *2) | *7) |

In the table, *1) is a ratio of residual (percent by weight), *2) is a colorless transparent solution, and *7) indicates that no peak of the oligomer and the high molecular compound was observed.

EXAMPLE 15

In the same glass vessel as described in Example 1, placed was 100 g of EHMA. Then, to the EHMA, added were p-methoxyphenol and acrylic acid (organic acid) respectively in amounts of 300 ppm and 50 ppm with respect to the EHMA to prepare a composition. Further, the oxygen in the gaseous phase portion in the glass vessel was adjusted to have a concentration of 21 volume percent. The resulting composition was observed to be colorless transparent solution. The mixed amount is shown in Table 5.

After sealing the glass vessel in which the resulting composition was placed, the glass vessel was placed still in a thermostatic bath at temperature of 50°±2° C. so as to avoid a direct sunlight. Under the described condition, changes in time of the EHMA, i.e., the stability thereof was evaluated. Namely, the stability of the EHMA was evaluated in the same manner as Example 1 except that the glass vessel was placed still so as to avoid a direct sunlight. The results are summarized in Table 6.

EXAMPLE 16

In the same glass vessel as described in Example 1, placed was 100 g of MHMA. Then, to the MHMA, added were p-t-butylcatechol, and acrylic acid (organic acid) respectively in amounts of 300 ppm and 100 ppm with respect to the MHMA to prepare a composition. Further, the oxygen in the gaseous phase portion of the glass vessel was adjusted to have a concentration of 21 volume percent. The resulting composition was observed to be colorless transparent solution. The mixed amount is shown in Table 5.

Next, using the resulting composition, the stability of the MHMA was evaluated in the same manner as in Example 15. The results are summarized in Table 6.

EXAMPLE 17

Example 15 was repeated except that in replace of acrylic acid, maleic acid (organic acid) was added to the EHMA in an amount of 50 ppm with respect to the EHMA to prepare a composition. The mixed amount is shown in Table 5. Next, using the resulting composition, the stability of the EHMA was evaluated in the same manner as in Example 15. The results are summarized in Table 6.

EXAMPLE 18

Example 15 was repeated except that in replace of acrylic acid, phenol (organic acid) was added to the EHMA in an amount of 300 ppm with respect to the EHMA to prepare a composition. The mixed amount is shown in Table 5. Next, using the resulting composition, the stability of the EHMA was evaluated in the same manner as in Example 15. The results are summarized in Table 6.

EXAMPLE 19

Example 15 was repeated except that water was added to the EHMA in an amount of 1,000 ppm with respect to the EHMA to prepare a composition. The mixed amount is shown in Table 5. Next, using the resulting composition, the stability of the EHMA was evaluated in the same manner as in Example 15. The results are summarized in Table 6.

TABLE 6

|  |  | after 4 weeks | after 8 weeks | | |
|---|---|---|---|---|---|
|  |  | *1) | *1) | appearance | GPC analysis result |
| Ex. | 15 | 100 | 98 | *2) | *7) |
|  | 16 | 100 | 97 | *2) | *7) |
|  | 17 | 100 | 98 | *2) | *7) |
|  | 18 | 100 | 96 | *2) | *11) |
|  | 19 | 100 | 99 | *2) | *7) |
| Com. Ex. | 2 | 100 | 89 | *4) | *9) |

In the table, *1) is a ratio of residual (percent by weight), *2) is a colorless transparent solution, *4) is slightly white turbid solution, *7) indicates that no peak of the oligomer and the high molecular compound was observed, *9) indicates that a peak of the oligomer was observed, and *11) indicates that a small peak of the oligomer was observed.

As is evident from the results shown in Tables 2, 4 and 6, the compositions obtained in Examples of the present invention showed superior properties over comparative compositions obtained in Comparative examples 1 to 4 in suppressing the generation of impurities and maintaining the quality thereof on storage for a long period of time. Namely, the stabilization method of the present invention offers an improved stability of the vinyl compound with hydroxy group.

It will be understood, however, that even though these numerous characteristics and advantages of the invention have been set forth in the foregoing description, together with details of the structure and function of the invention, the disclosure is illustrative only, and changes may be made in detail, especially in matters of shape, size and arrangement of the parts or in the sequence or the timing of the steps, within the broad principle of the present invention to the full extent indicated by the broad general meaning of the terms in which the appended claims are expressed.

What is claimed is:

1. A stabilization method for a vinyl compound with hydroxy group comprising the step of:

(a) coexisting a vinyl compound with hydroxy group of formula (1), a primary antioxidant, alcohol and/or

TABLE 5

|  |  | vinyl compound with hydroxy group | primary antioxidant*1) (ppm) | water*1) (ppm) | organic acid*1) (ppm) | oxygen concentration*2) |
|---|---|---|---|---|---|---|
| Ex | 15 | EHMA | p-methoxy phenol 300 | — | acrylic acid 50 | 21 |
|  | 16 | MHMA | p-t-butylcatechol 300 | — | acrylic acid 100 | 21 |
|  | 17 | EHMA | p-methoxy phenol 300 | — | maleic acid 50 | 21 |
|  | 18 | EHMA | p-methoxy phenol 300 | — | phenol 300 | 21 |
|  | 19 | EHMA | p-methoxy phenol 300 | 1,000 | acrylic acid 50 | 21 |
| Com. Ex | 2 | EHMA | p-methoxy phenol 300 | — | — | 21 |

In the Table, EHMA: ethyl α-(hydroxymethyl) acrylate, MHMA: methyl α-(hydroxymethyl) acrylate,
*1)amount with respect to the vinyl compound with hydroxy group
*2)volume percent water, $$CH_2=\underset{X}{C}-\underset{R}{CH}-OH \quad (1)$$

wherein R is a hydrogen atom or an organic residue, X is a —CN group, a —$COR_0$ group or a —$COOR_0$ group, and $R_0$ is a hydrogen atom or an organic residue and wherein said primary antioxidant is present in an amount of 10 ppm to 5,000 ppm with respect to the vinyl compound with hydroxy group.

2. The stabilization method as set forth in claim 1, wherein:
said alcohol and/or water is added in an amount of not less than 50 ppm with respect to said vinyl compound with hydroxy group.

3. The stabilization method as set forth in claim 1, wherein:
said alcohol and/or water is added in an amount ranging from 50 ppm to 5,000 ppm with respect to said vinyl compound with hydroxy group.

4. The stabilization method as set forth in claim 1, wherein:
said alcohol and/or water is added in an amount ranging from above $5 \times 10^{-3}$ times by weight to not more than 100 times by weight with respect to said vinyl compound with hydroxy group.

5. The stabilization method as set forth in claim 1, wherein:
said vinyl compound with hydroxy group is an acrylate compound.

6. The stabilization method as set forth in claim 1, wherein:
said primary antioxidant is a compound of at least one kind selected from the group consisting of p-methoxylphenol, p-t-butylcatechol, and phenothiazine.

7. The stabilization method as set forth in claim 1, wherein:
said primary antioxidant is added in an amount ranging from 10 ppm to 5,000 ppm with respect to said vinyl compound with hydroxy group.

8. The stabilization method as set forth in claim 1, wherein:
said step (a) includes the step of adding organic acid.

9. The stabilization method as set forth in claim 1, wherein:
said step (a) includes the step of adjusting an atmosphere to have a concentration of oxygen ranging from 1 to 30 volume percent.

10. A stabilization method for a vinyl compound with hydroxy group comprising the step of:
(a) coexisting a vinyl compound with hydroxy group of formula (1), a primary antioxidant, and an organic acid, $$CH_2=\underset{X}{C}-\underset{R}{CH}-OH \quad (1)$$

wherein R is a hydrogen atom or an organic residue, X is a —CN group, a —$COR_0$ group or a —$COOR_0$ group, and $R_0$ is a hydrogen atom or an organic residue and wherein said primary antioxidant is present in an amount of 10 ppm to 5,000 ppm with respect to the vinyl compound with hydroxy group.

11. The stabilization method as set forth in claim 10, wherein:
said organic acid is added in an amount of not less than 10 ppm with respect to said vinyl compound with hydroxy group.

12. The stabilization method as set forth in claim 10, wherein:
said organic acid is added in an amount ranging from 10 ppm to 5,000 ppm with respect to said vinyl compound with hydroxy group.

13. The stabilization method as set forth in claim 10, wherein:
said vinyl compound with hydroxy group is an acrylate compound.

14. The stabilization method as set forth in claim 10, wherein:
said primary antioxidant is a compound of at least one kind selected from the group consisting of p-methoxylphenol, p-t-butylcatechol, and phenothiazine.

15. The stabilization method as set forth in claim 10, wherein:
said primary antioxidant is added in an amount ranging from 10 ppm to 5,000 ppm with respect to said vinyl compound with hydroxy group.

16. The stabilization method as set forth in claim 10, wherein:
said step (a) includes the step of adding alcohol and/or water.

17. The stabilization method as set forth in claim 10, wherein:
said step (a) includes the step of adjusting an atmosphere to have a concentration of oxygen ranging from 1 to 30 volume percent.

18. A composition comprising:
a vinyl compound with hydroxy group of formula (1); a primary antioxidant; and alcohol and/or water, $$CH_2=\underset{X}{C}-\underset{R}{CH}-OH \quad (1)$$

wherein R is a hydrogen atom or an organic residue, X is a —CN group, a —$COR_0$ group or a —$COOR_0$ group, and $R_0$ is a hydrogen atom or an organic residue and wherein said primary antioxidant is present in an amount of 10 ppm to 5,000 ppm with respect to the vinyl compound with hydroxy group.

19. The composition as set forth in claim 18, wherein:
said alcohol and/or water is contained in an amount of not less than 50 ppm with respect to said vinyl compound with hydroxy group.

20. The composition as set forth in claim 18, wherein:
said alcohol and/or water is contained in an amount ranging from 50 ppm to 5,000 ppm with respect to said vinyl compound with hydroxy group.

21. The composition as set forth in claim 18, wherein:
said alcohol and/or water is contained in an amount ranging from above $5 \times 10^{-3}$ times by weight to not more than 100 times by weight with respect to said vinyl compound with hydroxy group.

22. The composition as set forth in claim 18, wherein:
said vinyl compound with hydroxy group is an acrylate compound.

23. The composition as set forth in claim 18, wherein:
said primary antioxidant is a compound of at least one kind selected from the group consisting of p-methoxylphenol, p-t-butylcatechol, and phenothiazine.

24. The composition as set forth in claim 18, wherein:
said primary antioxidant is contained in an amount ranging from 10 ppm to 5,000 ppm with respect to said vinyl compound with hydroxy group.

25. The composition as set forth in claim 18, further comprising:
organic acid.

26. A composition comprising:
a compound with hydroxy group of formula (1);
a primary antioxidant; and
an organic acid,

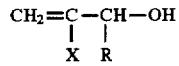
 (1)

wherein R is a hydrogen atom or an organic residue, X is a —CN group, a —$COR_0$ group or a —$COOR_0$ group, and $R_0$ is a hydrogen atom or an organic residue and wherein said primary antioxidant is present in an amount of 10 ppm to 5,000 ppm with respect to the vinyl compound with hydroxy group.

27. The composition as set forth in claim 26, wherein:
said organic acid is contained in an amount of not less than 10 ppm with respect to said vinyl compound with hydroxy group.

28. The composition as set forth in claim 26, wherein:
said organic acid is contained in an amount ranging from 10 ppm to 5,000 ppm with respect to said vinyl compound with hydroxy group.

29. The composition as set forth in claim 26, wherein:
said vinyl compound with hydroxy group is an acrylate compound.

30. The composition as set forth in claim 26, wherein:
said primary antioxidant is a compound of at least one kind selected from the group consisting of p-methoxylphenol, p-t-butylcatechol, and phenothiazine.

31. The composition as set forth in claim 26, wherein:
said primary antioxidant is contained in an amount ranging from 10 ppm to 5,000 ppm with respect to said vinyl compound with hydroxy group.

32. The composition as set forth in claim 26, further comprising:
alcohol and/or water.

* * * * *